US006789748B2

(12) United States Patent
Noestheden

(10) Patent No.: US 6,789,748 B2
(45) Date of Patent: Sep. 14, 2004

(54) WATER JET

(75) Inventor: Andrew Noestheden, Tecumseh (CA)

(73) Assignee: Valiant Corporation, Windsor (CA)

(*) Notice: Subject to any disclaimer, the term of this patent is extended or adjusted under 35 U.S.C. 154(b) by 451 days.

(21) Appl. No.: 09/783,260

(22) Filed: Feb. 14, 2001

(65) Prior Publication Data

US 2002/0109020 A1 Aug. 15, 2002

(51) Int. Cl.[7] .............................................. A61M 11/02
(52) U.S. Cl. ........................ 239/373; 239/346; 239/340
(58) Field of Search ................................ 139/337, 340, 139/346, 347, 373; 137/199

(56) References Cited

U.S. PATENT DOCUMENTS 2,281,283 A * 4/1942 Haast ......................... 137/199
2,862,513 A * 12/1958 Mercier et al. .......... 137/115.11
2,893,716 A * 7/1959 Smith ......................... 239/373
3,147,923 A * 9/1964 Smalley ...................... 239/373
3,771,176 A * 11/1973 Herman, Sr. ................. 4/578.1
4,381,645 A * 5/1983 Galuska ...................... 137/147
4,723,710 A * 2/1988 Lucore, II .................. 239/124
4,765,537 A * 8/1988 Donovan .................... 137/202
4,846,214 A * 7/1989 Strong ........................ 137/199
4,951,701 A * 8/1990 Boehmer .................... 137/199
5,221,026 A * 6/1993 Williams .................... 137/606
5,810,213 A * 9/1998 Flores et al. ................ 239/373
6,056,208 A * 5/2000 Pirker et al. ................ 239/119

* cited by examiner

*Primary Examiner*—Christopher S. Kim
(74) *Attorney, Agent, or Firm*—Gifford, Krass, Groh, Sprinkle, Anderson & Citkowski, P.C.

(57) ABSTRACT

A water jet is disclosed having a tank which forms a reservoir containing a liquid, such as water. An elongated conduit has one end fluidly connected to the reservoir while a nozzle is connected to the other end of the conduit. This nozzle, furthermore, has an opening with a cross-sectional area less than the cross-sectional area of the conduit. A valve is connected in series between the conduit and the reservoir, and this valve is movable between an open and a closed position. The reservoir is pressurized to a pressure in the range of 30–300 psi so that, once the valve is opened, water flows through the conduit and out through the nozzle at a high pressure and high speed water jet. This water jet can be used, inter alia, to clean industrial parts, such as engine blocks.

3 Claims, 2 Drawing Sheets

WATER JET

BACKGROUND OF THE INVENTION

I. Field of the Invention

The present invention relates generally to a high speed/high pressure water jet.

II. Description of Related

There are many previously known water jets that are used for a variety of purposes. These water jets produce water pressure in the form a high speed and high pressure jet which is used in many applications, such as cleaning applications, as well as cutting applications.

In order to form the high pressure water jet, these previously known devices have traditionally used a high pressure pump which, in turn, requires a powerful engine in order to power the pump. Such high pressure pumps oftentimes require engines having a power of 150 horsepower, or even more.

Since these previously known water jets have required massive high pressure pumps as well as powerful engines to drive the pumps, these water jets are expensive not only to manufacture and acquire, but also to operate.

In view of the shortcomings of high speed/high pressure water jets, low pressure water jets are frequently used in applications such as cleaning industrial parts, such as engine blocks, crankshafts and the like. However, these previously known low speed/low pressure water jets are unable to achieve the complete removal of metal shavings from some industrial parts, such as engine blocks.

SUMMARY OF THE PRESENT INVENTION

The present invention provides a water jet which overcomes all of the above-mentioned disadvantages of the previously known devices and is particularly useful for the washing or removal of metal shavings from industrial parts, such as engine blocks.

In brief, the water jet of the present invention comprises a tank forming a reservoir which is filled with a liquid, such as water. An elongated conduit has one end fluidly connected to the reservoir and a nozzle connected to the other end of the conduit. This nozzle, furthermore, has a cross-sectional opening smaller than the cross-sectional opening of the conduit and preferably less than one one-hundredth the cross-sectional area of the conduit.

A valve is connected in series between the reservoir and the conduit, and this valve is movable between an open and a closed position. The reservoir, furthermore, is pressurized by air pressure in the range of 30–300 psi. Consequently, as the valve is moved to its open position, the air pressure from the reservoir pumps water from the reservoir down through the conduit and towards the nozzle. As this water flow reaches the nozzle, the reduced area opening of the nozzle translates the water flow through the conduit into a high speed water jet. This water jet, in turn, can be used for many applications, such as cleaning industrial parts.

In order to preclude or at least minimize the turbulence of the water flow through the conduit upon opening of the valve, an air bleed circuit is preferably connected to the conduit adjacent or at the nozzle. This air bleed circuit bleeds air from the conduit during the flow of water through the conduit and towards the nozzle and minimizes turbulence of the water flow through the conduit that might otherwise be caused by air entrapped within the conduit. Furthermore, in one embodiment of the invention, the air bleed circuit includes a vacuum pump to actively evacuate air from the conduit.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
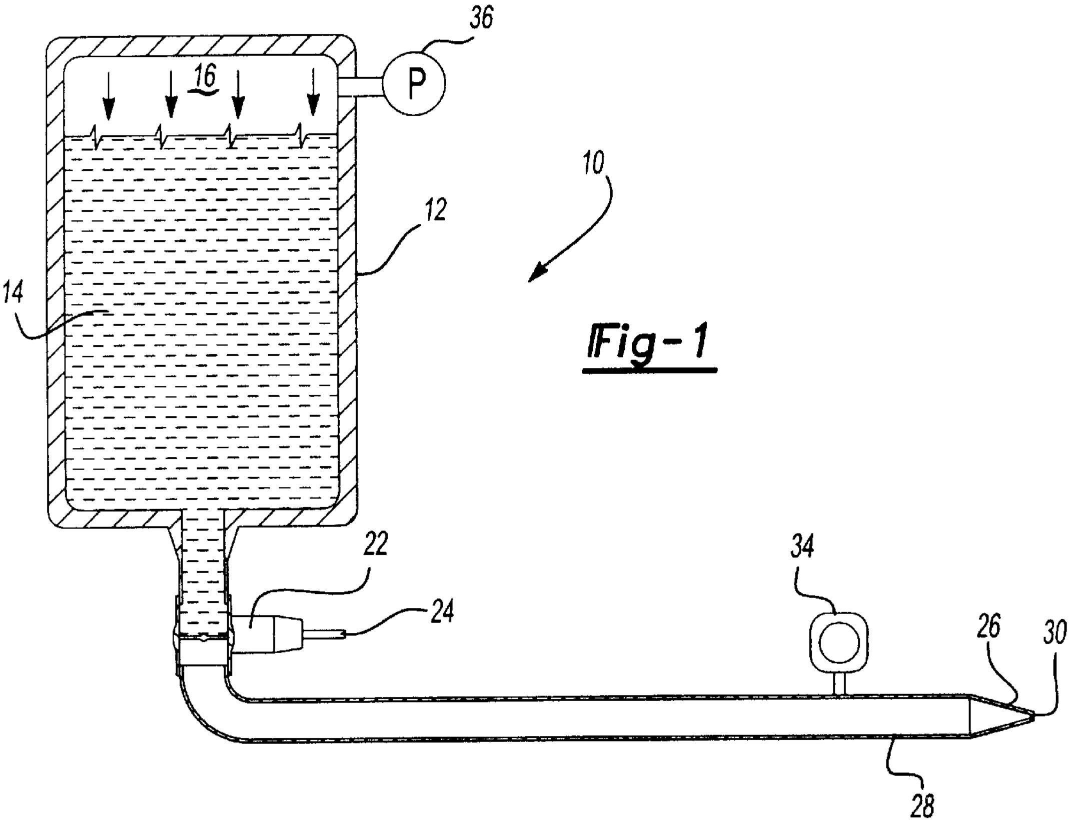
FIG. 1 is a side sectional view illustrating a preferred embodiment of the present invention.

With reference first to FIG. 1, a preferred embodiment of the water jet 10 of the present invention is there shown and comprises a tank 12 which forms a reservoir 14. The reservoir 14 is filled with a liquid, typically water, to the extent that an air pocket 16 is formed at the upper portion of the tank 12.

An elongated conduit 18 has one end 20 connected to the reservoir 14. A valve 22 is fluidly connected in series between the end 20 of the conduit 18 and the reservoir 14. Preferably, this valve 22 is a gate valve and actuated by an actuator 24 between an open position and a closed position. In its closed position (FIG. 1), the gate valve 22 prevents fluid flow from the reservoir 14 through the conduit while, conversely, in its open position (FIG. 2), the valve 22 allows fluid to freely flow from the reservoir 14 and through the conduit 18.

Still referring to FIG. 1, a nozzle 26 is secured to the other end 28 of the conduit 18. This nozzle 26 has an opening 30 which is smaller in cross-sectional area than the cross-sectional area of the conduit 18. Preferably, the area of the nozzle opening 30 is in the range of one one-hundredth the cross-sectional area of the conduit 18.

The conduit 18 extends in substantially a straight line from the valve 22 and to the nozzle 26 in order to minimize turbulence of the water flow through the conduit 18. Additionally, an air bleed circuit 34 is fluidly connected to the interior of the conduit 18 either at or adjacent the nozzle 26. This air bleed circuit 34 bleeds air from the conduit 18 during water flow through the conduit 18. The air bleed circuit 34, furthermore, may include a vacuum pump which actively evacuates the interior of the conduit 18 of air.

Still referring to FIG. 1, an air pressurization means 36, such as an air pump, pressurizes the air pocket 16 in the tank 12 to a predetermined pressure. Preferably, this pressure is in the range of 30–300 psi. Additionally, the cross-sectional area of the tank 12 is preferably several times the cross-sectional area of the conduit 18 so that the effective pressure at the end 20 of the conduit 18 is several times the pressure of the air pocket 16.

Figure 2:
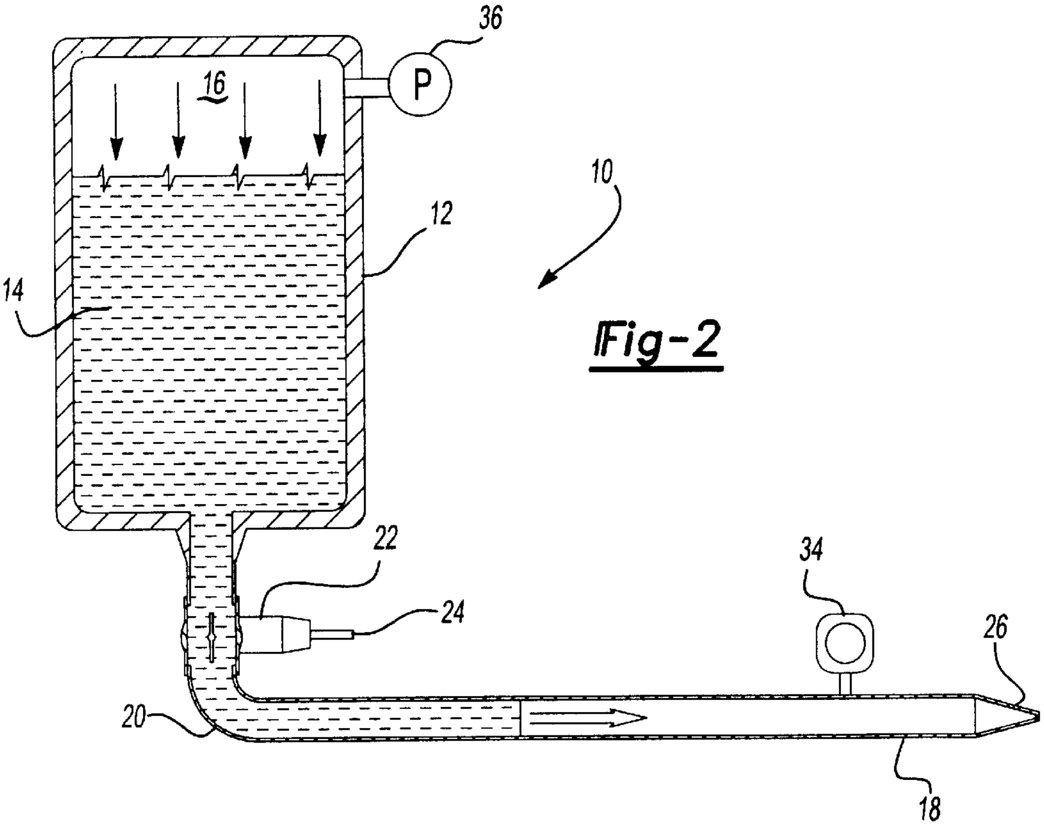
FIG. 2 is a view similar to FIG. 1 but illustrating the operation of the invention following the initial opening of the valve.

With reference now to FIGS. 1 and 2, when activation of the water jet is desired, the valve 22 is moved from its closed position (FIG. 1) to its open position (FIG. 2). In doing so, the water or other liquid contained within the reservoir 14 flows downwardly through the valve 22 and into the conduit 18. The flow of water through the conduit 18 will accelerate through the conduit 18 and thus form a wall of water within the interior of the conduit 18 as shown in FIG. 2. Simultaneously as the water flows through the conduit 18, the air bleed circuit 34 removes air from the interior of the conduit so that the air within the conduit neither cushions the water flow through the conduit 18 nor creates turbulence of the water flow through the conduit.

Figure 3:
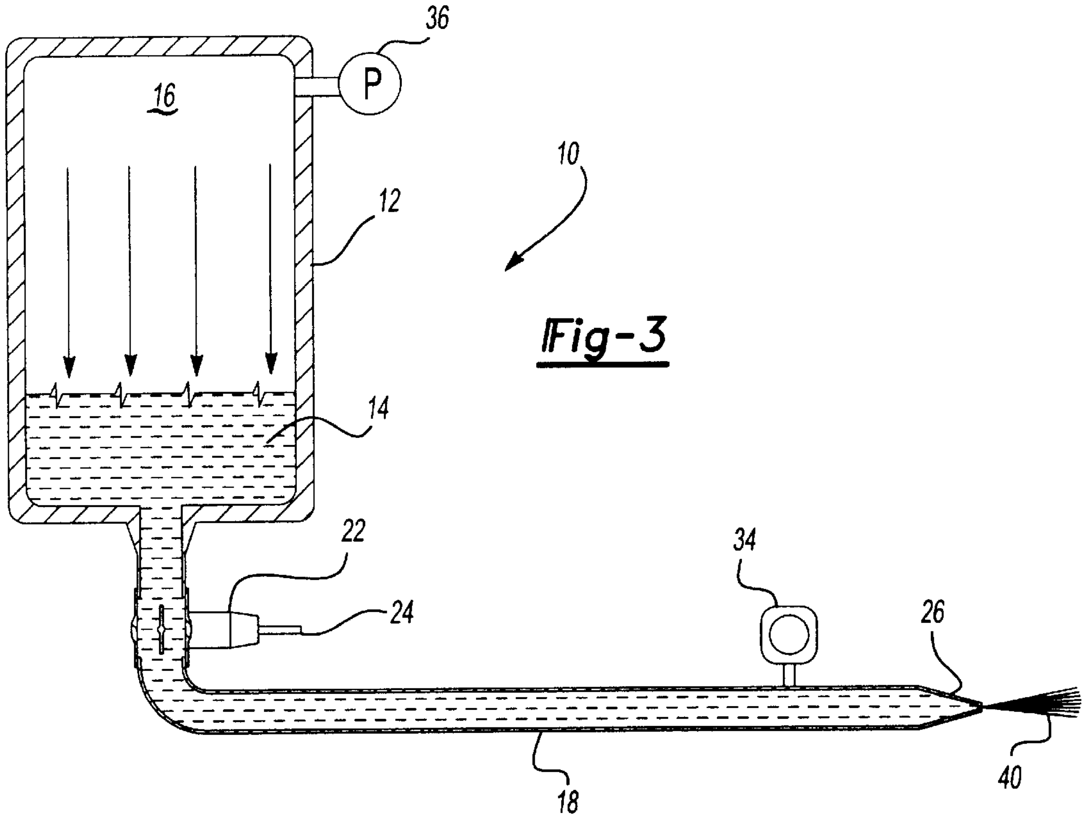
FIG. 3 is a view similar to FIG. 2 and further illustrating the operation of the preferred embodiment of the present invention.

With reference now to FIG. 3, as the water flow through the conduit 18 and impacts the nozzle 26, the nozzle 26 reduces the water flow from the cross-sectional area of the conduit 18 and to the reduced area of the nozzle opening 30. This in turn creates a high speed, high pressure water jet 40 at the nozzle opening 30.

Figure 4:
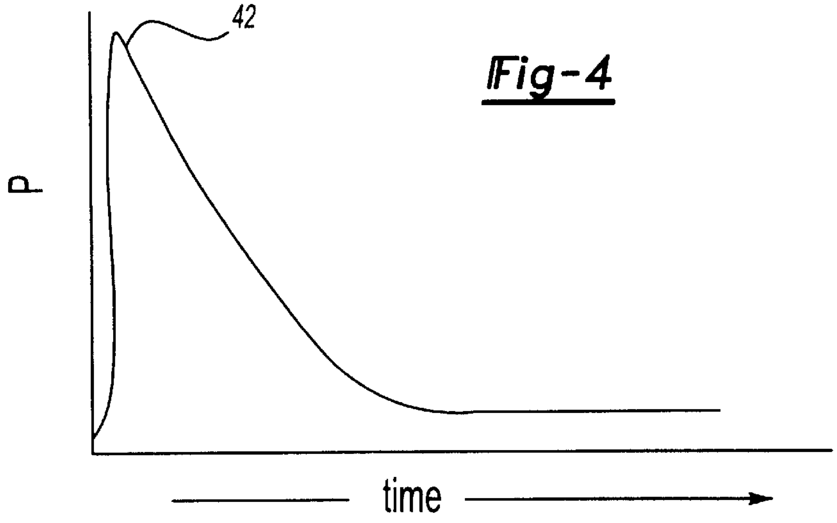
FIG. 4 is a graph illustrating the operation of the preferred embodiment of the present invention.

With reference now to FIG. 4, a graph illustrating the pressure of the water jet 40 as a function of time is illustrated. As shown in FIG. 4, as the water flow through the conduit 18 initially hits the nozzle 26, an extremely high pressure, e.g. 10,000 psi, is created at the water jet 40 as indicated at point 42 in FIG. 4. Thereafter, the pressure of the water jet 40 diminishes until the cycle is completed.

One practical application for the water jet 10 of the present invention is to clean industrial parts, such as engine blocks, of metal filings and other debris. For example, assuming that the conduit 18 has an inside diameter of four inches and the nozzle opening 30 has a diameter of five-sixteenths of an inch, a pressurization of about 150 psi in the air pocket 16 of the tank 12 causes the water flow through the conduit 18 to reach a speed of about 55 miles per hour in approximately six feet or straight section of the conduit 18. This water flow translates to a pressure of approximately 10,000 psi at the water jet 40. Thus, when the water jet 10 is used to clean industrial parts, the high initial pressure from the water jet is sufficient to dislodge any shavings that may be entrapped within passageways of the industrial parts, such as engine blocks, and thereafter flush out any debris or metal shavings from the industrial part.

From the foregoing, it can be seen that the present invention provides a simple and yet highly effective water jet. Having described my invention, however, many modifications thereto will become apparent to those skilled in the art to which it pertains without deviation from the spirit of the invention as defined by the scope of the appended claims.

I claim:

1. A liquid jet comprising:

a tank forming a reservoir, said reservoir being filled with a liquid, an elongated conduit having one end fluidly connected to said reservoir, a nozzle connected to the other end of said conduit, said nozzle having an opening with a cross-sectional area less than the cross-sectional area of said conduit, a gate valve connected in series between said one end of said conduit and said reservoir, said gate valve being movable between an open position in which liquid freely flows from said reservoir through said conduit and a closed position in which said gate valve prevents fluid flow from said reservoir into said conduit, means for pressurizing said reservoir to a predetermined pressure, means for actuating said gate valve between said open and said closed position, and means for removing air from an interior of said conduit following movement of said valve to said open position and as said liquid from said reservoir flows past said gate valve and towards said nozzle, said removing means comprising an air bleed fluid circuit fluidly connected to said conduit adjacent said nozzle downstream from said gate valve.

2. The invention as defined in claim 1 wherein said area of said nozzle opening is less than one one-hundredth the cross-sectional area of said conduit.

3. The invention as defined in claim 1 wherein said predetermined pressure is in the range of 30–300 psi.

* * * * *